United States Patent
Jeon

(10) Patent No.: US 11,260,062 B2
(45) Date of Patent: Mar. 1, 2022

(54) PHARMACEUTICAL COMPOSITION FOR TREATMENT OF LUNG CANCER COMPRISING GLUCOCORTICOID-BASED COMPOUND

(71) Applicant: AJOU UNIVERSITY INDUSTRY-ACADEMIC COOPERATION FOUNDATION, Suwon-si (KR)

(72) Inventor: Sang-Min Jeon, Suwon-si (KR)

(73) Assignee: AJOU UNIVERSITY INDUSTRY-ACADEMIC COOPERATION FOUNDATION, Suwon-si (KR)

(*) Notice: Subject to any disclaimer, the term of this patent is extended or adjusted under 35 U.S.C. 154(b) by 0 days.

(21) Appl. No.: 15/772,714

(22) PCT Filed: Nov. 2, 2016

(86) PCT No.: PCT/KR2016/012534
§ 371 (c)(1),
(2) Date: May 1, 2018

(87) PCT Pub. No.: WO2017/078405
PCT Pub. Date: May 11, 2017

(65) Prior Publication Data
US 2019/0201416 A1 Jul. 4, 2019

(30) Foreign Application Priority Data

Nov. 2, 2015 (KR) .................. 10-2015-0153296
Oct. 18, 2016 (KR) .................. 10-2016-0135006

(51) Int. Cl.
A61K 31/573 (2006.01)
A61P 35/00 (2006.01)
A61K 31/404 (2006.01)
A61K 31/436 (2006.01)

(52) U.S. Cl.
CPC .......... *A61K 31/573* (2013.01); *A61K 31/404* (2013.01); *A61K 31/436* (2013.01); *A61P 35/00* (2018.01)

(58) Field of Classification Search
USPC ...................................................... 514/171
See application file for complete search history.

(56) References Cited

FOREIGN PATENT DOCUMENTS

CN           103705922 A      4/2014
KR    10-2008-0018150 A      2/2008

OTHER PUBLICATIONS

Singh (Dysfunctional KEAP1-nrf2 Interactionin Non-Small-Cell Lung Cancer, PLoS Med, Oct. 2006; 3(10).*
Greenbert (Glucocorticoid Inhibit Lung Cancer Cell Growth through Both the Extracellular Signal-Related Kinase Pathway and Cell Cycle Regulators, Am J Respiration, Cell Mol. Biol, vol. 27, 2002, pp. 320-328).*
Califano, (Expert Consensus on the Managementof of Adverse Events from EGFR Tryosine Kinase Inhibitors in the UK, Drugs, Jul. 2015, 75; p. 135-1348).*
Sporn (NRF2 and cancer: the good, the bad and the importance of context, Nat Rev Cancer. ; 12(8), 2011: . doi:10.1038/nrc3278, pp. 1-24).*
Greenberg et al., "Glucocorticoids Inhibit Lung Cancer Cell Growth through Both the Extracellular Signal-Related Kinase Pathway and Cell Cycle Regulators", Am. J. Respir. Cell Mol. Biol., vol. 27, pp. 320-328, (2002).
Gridelli et al., "The Potential Role of mTOR Inhibitors in Non-Small Cell Lung Cancer", The Oncologist, vol. 13, pp. 139-147, (2008).
Honma et al., "Vesnarinone and glucocorticoids cooperatively induce G1 arrest and have an anti-tumour effect on human non-small cell lung carcinoma cells grown in nude mice", British Journal of Cancer, vol. 80, 1/2, pp. 96-103, (1999).
Kaufman et al., "LKB1 Loss Induces Characteristic Patterns of Gene Expression in Human Tumors Associated with NRF2 Activation and Attenuation of PI3K-AKT", Journal of Thoracic Oncology, vol. 9, No. 6, pp. 794-804, (2014).
Skoulidis et al., "Co-occurring Genomic Alterations Define Major Subsets of KRAS-Mutant Lung Adenocarcinoma with Distinct Biology, Immune Profiles, and Therapeutic Vulnerabilities", Cancer Discovery, vol. 5, No. 8, pp. 360-877, (2015).

(Continued)

*Primary Examiner* — Kathrien A Cruz
(74) *Attorney, Agent, or Firm* — Vorys, Sater, Seymour & Pease LLP; Mih Suhn Koh

(57) ABSTRACT

Provided is a composition for treating or ameliorating lung cancer including a glucocorticoid-based compound, a glucocorticoid-based compound and an mTOR inhibitor, or a glucocorticoid-based compound and an AMPK inhibitor as an active ingredient. The glucocorticoid-based compounds inhibit the growth of cancer cells by suppressing NRF2 in KEAP1 mutant lung cancer or KEAP1 and LKB1 mutant lung cancer, and exhibit a more potent anticancer effect when used in combination with the mTOR inhibitor, and thus the compounds can be effectively used as anticancer agents for mutant lung cancer. Further, the glucocorticoid-based compounds exhibit a strong anticancer synergistic effect in a low nutritional state when treated in combination with an AMPK inhibitor in KEAP1 and LKB1 normal lung cancer, and thus the compounds can also be used as an anticancer agent for KEAP1 normal lung cancer.

7 Claims, 8 Drawing Sheets
Specification includes a Sequence Listing.

(56) References Cited

OTHER PUBLICATIONS

Socinski, "The Current Status and Evolving Role of Sunitinib in Non-small Cell Lung Cancer", Journal of Thoracic Oneology, vol. 3, No. 6, Suppl. 2, pp. S119-S123, (2008).
Kratschmar et al., "Suppression of the Nrf2-Dependent Antioxidant Response by Glucocorticoids and 11beta-HSD1-Mediated Glucocorticoid Activation in Hepatic Cells", PLoS ONE, 2012, vol. 7, Issue 5, e36774, 14 pages.
Chinese Office Action issued in corresponding Chinese Patent Application No. CN201680064090.8, 5 pages, dated Jun. 16, 2020.
Notice of Allowance issued in corresponding Korean Patent Application No. 10-2016-0135006, 5 pages, dated Jul. 5, 2018.

* cited by examiner

FIG. 2a

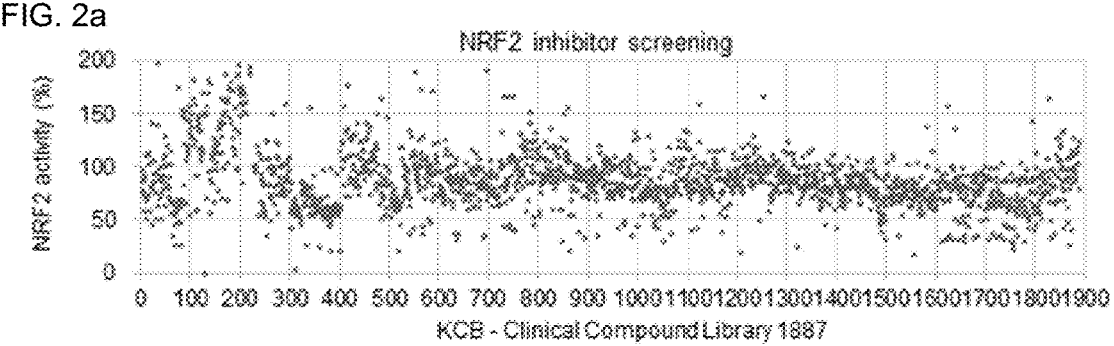

FIG. 2b

| 1uM 24hr | NRF2 activity (%) | |
|---|---|---|
| 글루코코르티코이드 | Mean | SD |
| Clobetasol propionate | 31.74 | 2.57 |
| Triamcinolone acetonide | 33.14 | 0.96 |
| Beclomethasone dipropionate | 33.22 | 5.25 |
| Betamethasone valerate | 34.38 | 0.74 |
| Flumethasone | 34.43 | 0.70 |
| Flurandrenolide | 35.41 | 1.41 |
| Hydrocortisone valerate | 35.61 | 2.63 |
| Flunisolide | 35.69 | 1.91 |
| Desonide | 36.71 | 3.46 |
| Clocortolone pivalate | 37.31 | 0.89 |
| Budesonide | 37.48 | 0.63 |
| Prednisolone hemisuccinate | 37.54 | 1.45 |
| Desoxymetasone | 37.64 | 3.06 |
| Hydrocortisone butyrate | 38.75 | 1.09 |
| Betamethasone sodium phosphate | 38.36 | 2.35 |
| Hydrocortisone | 39.47 | 0.87 |
| Diflorasone diacetate | 39.92 | 3.05 |
| Prednisolone sodium phosphate | 40.00 | 1.08 |
| Prednicarbate | 41.36 | 3.87 |
| Triamcinolone | 42.51 | 3.53 |
| Methylprednisolone sodium succinate | 43.12 | 2.14 |
| Mometasone furoate | 43.27 | 1.32 |
| Triamcinolone diacetate | 43.34 | 3.38 |
| Rimexolone | 44.70 | 1.61 |
| Isoflupredone acetate | 44.95 | 3.58 |
| Betamethasone | 45.05 | 2.59 |
| Dexamethasone acetate | 45.80 | 1.14 |
| Melengestrol acetate | 45.97 | 2.47 |
| Fluticasone propionate | 46.20 | 5.13 |
| Prednisolone | 46.64 | 2.36 |
| Methylprednisolone, 6-alpha | 46.72 | 3.98 |
| Amcinonide | 48.47 | 1.79 |
| Hydrocortisone base | 58.28 | 4.03 |
| Fluorometholone | 58.29 | 4.71 |
| Finasteride | 59.29 | 0.57 |
| Fluocinonide | 60.90 | 3.34 |
| Cortisol acetate | 63.51 | 1.82 |

FIG. 5a 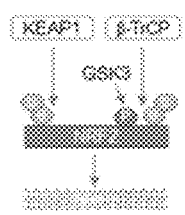 FIG. 5b 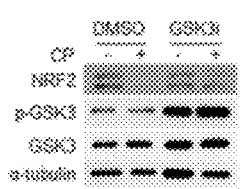 FIG. 5c 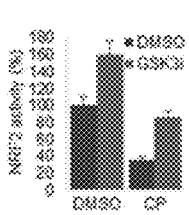 FIG. 5d 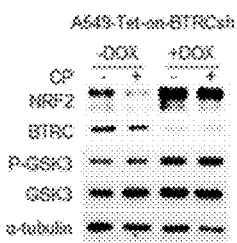

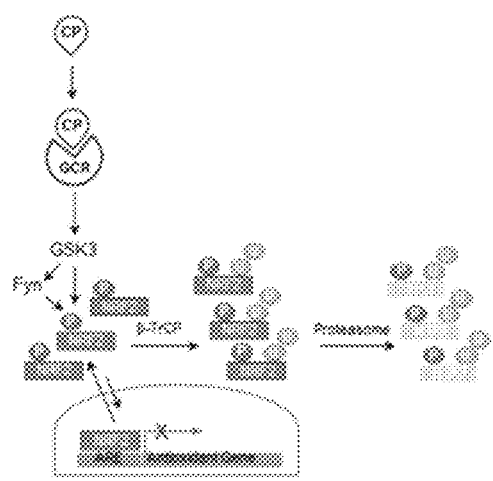
FIG. 5f  FIG. 5g  FIG. 5h
FIG. 6a 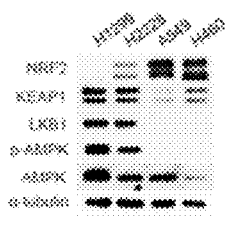 FIG. 6b 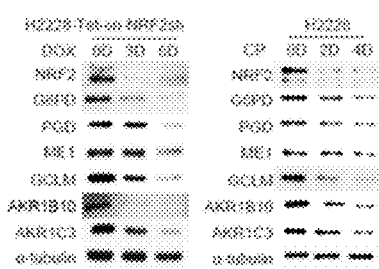 FIG. 6c 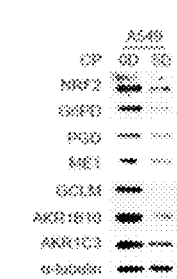 FIG. 6d 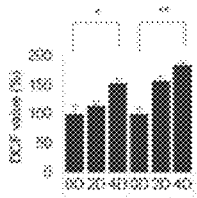

PHARMACEUTICAL COMPOSITION FOR TREATMENT OF LUNG CANCER COMPRISING GLUCOCORTICOID-BASED COMPOUND

SEQUENCE LISTING

The Sequence Listing submitted in text format (.txt) filed on Sep. 24, 2018, named "Sequence Listing", created on Sep. 21, 2018 (1.35 KB), is incorporated herein by reference.

TECHNICAL FIELD

The present invention relates to compositions for treating lung cancer.

BACKGROUND ART

Lung cancer is the second most common cancer in both men and women and accounts for 15% of all cancers. According to the report by the American Cancer Society in 2011, at least 220,000 patients are diagnosed with lung cancer per a year, of which about 70% reaches death, taking up 27% of all cancer deaths.

Among these lung cancers, non-small cell lung cancer is a type of carcinoma, which refers to all epithelial lung cancer that is not small lung cancer and accounts for approximately 85% to 90% of total lung cancer. Symptoms of non-small cell lung cancer include persistent cough, chest pain, weight loss, nail damage, joint pain and shortness of breath, etc. Because non-small cell lung cancer usually progresses slowly, it is difficult to find and treat it at early stage, and it is highly likely to be detected only after transferring to the whole body including bone, liver, small intestine and brain, etc.

Non-small cell lung cancer, which is relatively less sensitive to chemotherapy comparing to small cell lung cancer, can be divided into cancer stages according to the TNM classification as follows: the size of tumor, the diffusion degree into regional lymph node and presence or absence of metastasis.

In the early non-metastatic non-small cell lung cancer of non-small cell lung cancer, the sensitivity to chemotherapy and radiation is very low and thus a surgery together with ancillary chemotherapy associated with cisplatin containing platinum is required. On the other hand, when passing by the early stage and developed to metastatic non-small cell lung cancer, various chemotherapy and radiotherapy are performed.

Also, non-small cell lung cancer is classified into several subtypes according to size, morphology and chemical composition of cancer cells and typical examples thereof are adenocarcinoma, squamous cell carcinoma, large cell carcinoma, and the like. Adenocarcinoma is the most frequently occurring lung cancer, accounting for at least 40% of all lung cancers and it is found in an outer region of the lungs and tends to progress more slowly than other lung cancers, but exhibits an early high metastatic tendency and radioactive resistance. Squamous cell carcinoma is a type of non-small cell lung cancer that accounts for 25% to 30% of all lung cancers. It starts in the early version of airway cells and high incidence exhibits in smokers. In addition, large cell carcinoma, which accounts for 10% to 15% of all lung cancers, can develop anywhere in the lung and its rate of progression is fast comparatively enough to that of small cell lung cancer. However, despite these high incidence and mortality rates, no drugs or treatment methods have yet been developed to overcome non-small cell lung cancer.

Meanwhile, since the finding of tumorigenesis and suppression genes in the 1970s and 1980s, novel tumor-specific mutant genes and target anticancer therapy targeting signal transduction pathways have been actively researched. Recently, as part of its strategy, large-scale tumor genome projects (TCGA, ICGC, CGP) have been conducted centering on the United States and the United Kingdom. As a result, inhibitors of epidermal growth factor receptor (EGFR), vascular endothelial growth factor (VEGF (R)), and mTOR (mechanistic targets of rapamycin), which targets specific signal transduction pathway, have been developed with much expectation, but they have not been as effective as expected. It seems because of the diverse and heterogeneous mutations which are identified by the tumor genome project and diversity and the heterogeneity of the abnormal signaling pathways.

Recently, many attempts have been made to develop effective combination chemotherapy to overcome the limit of this target anticancer therapy. To this end, studies have been conducted to identify combinations of gene mutations commonly found in cancer. In recent years, in non-small cell lung cancer, mutation of KEAP1 (kelch-like ECH-associated protein 1) gene and mutation of LKB1 (liver kinase B1, liver kinase B1) have been reported to frequently occur together. The KEAP1 mutation induces the activation of NRF2 (nuclear factor (erythroid-derived 2)-like 2 and inhibition of NFR2 expression in KEAP1 mutant lung cancer has been reported to effectively inhibit the growth of cancer cells, thus the development of NFR2 inhibitors is greatly demanded. However, several NRF2 inhibitors found through natural product screening have been reported, but the effect is insignificant and inconsistent, and no drugs are currently under clinical development. Meanwhile, LKB1 mutation induces the activation of mTORC1, and various drugs including rapamycin have been developed as inhibitors of mTORC1. Therefore, a combined anticancer therapy which inhibits both NRF2 and mTORC1, which are activated in non-small cell lung cancer in which KEAP1 and LKB1 are mutated together, is expected to be very effective, but no specific research has been conducted.

DISCLOSURE

Technical Problem

It is an object of the present invention to provide a pharmaceutical composition for treating lung cancer, which inhibits NRF2 activity which is frequently activated in lung cancer.

It is another object of the present invention to provide a health functional food composition for improving lung cancer, which inhibits NRF2 activity which is frequently activated in lung cancer.

Technical Solution

To achieve the object of the present invention, the present invention provides a pharmaceutical composition for treating lung cancer comprising at least a glucocorticoid-based compound selected from the group consisting of clobetasol propionate, amcinonide, betamethasone valerate, hydrocortisone valerate, flunisolide, flurandrenolide, flumethasone, desonide, beclomethasone dipropionate, triamcinolone acetonide, budesonide, mometasone furoate, desoxymetasone, clocortolone pivalate, prednisolone hemisuccinate, hydrocortisone butyrate, betamethasone sodium phosphate, hydrocortisone, diflorasone diacetate, prednisolone sodium phosphate, prednicarbate, triamcinolone, methylprednisolone sodium succinate, triamcinolone diacetate, rimexolone, isoflupredone acetate, betamethasone, dexamethasone acetate, melengestrol acetate, fluticasone propionate, prednisolone, methylprednisolone 6-alpha, hydrocortisone base, fluorometholone, finasteride, fluocinonide and cortisol acetate.

Also, the present invention provides a pharmaceutical composition for treating lung cancer comprising: at least a glucocorticoid-based compound selected from the group consisting of clobetasol propionate, amcinonide, betamethasone valerate, hydrocortisone valerate, flunisolide, flurandrenolide, flumethasone, desonide, beclomethasone dipropionate, triamcinolone acetonide, budesonide, mometasone furoate, desoxymetasone, clocortolone pivalate, prednisolone hemisuccinate, hydrocortisone butyrate, betamethasone sodium phosphate, hydrocortisone, diflorasone diacetate, prednisolone sodium phosphate, prednicarbate, triamcinolone, methylprednisolone sodium succinate, triamcinolone diacetate, rimexolone, isoflupredone acetate, betamethasone, dexamethasone acetate, melengestrol acetate, fluticasone propionate, prednisolone, methylprednisolone 6-alpha, hydrocortisone base, fluorometholone, finasteride, fluocinonide and cortisol acetate; and a mTOR inhibitor.

In addition, the present invention provides a pharmaceutical composition for treating lung cancer comprising: at least a glucocorticoid-based compound selected from the group consisting of clobetasol propionate, amcinonide, betamethasone valerate, hydrocortisone valerate, flunisolide, flurandrenolide, flumethasone, desonide, beclomethasone dipropionate, triamcinolone acetonide, budesonide, mometasone furoate, desoxymetasone, clocortolone pivalate, prednisolone hemisuccinate, hydrocortisone butyrate, betamethasone sodium phosphate, hydrocortisone, diflorasone diacetate, prednisolone sodium phosphate, prednicarbate, triamcinolone, methylprednisolone sodium succinate, triamcinolone diacetate, rimexolone, isoflupredone acetate, betamethasone, dexamethasone acetate, melengestrol acetate, fluticasone propionate, prednisolone, methylprednisolone 6-alpha, hydrocortisone base, fluorometholone, finasteride, fluocinonide and cortisol acetate; and an AMPK inhibitor.

To achieve another object of the present invention, the present invention provides a health functional food composition for improving lung cancer comprising at least a glucocorticoid-based compound selected from the group consisting of clobetasol propionate, amcinonide, betamethasone valerate, hydrocortisone valerate, flunisolide, flurandrenolide, flumethasone, desonide, beclomethasone dipropionate, triamcinolone acetonide, budesonide, mometasone furoate, desoxymetasone, clocortolone pivalate, prednisolone hemisuccinate, hydrocortisone butyrate, betamethasone sodium phosphate, hydrocortisone, diflorasone diacetate, prednisolone sodium phosphate, prednicarbate, triamcinolone, methylprednisolone sodium succinate, triamcinolone diacetate, rimexolone, isoflupredone acetate, betamethasone, dexamethasone acetate, melengestrol acetate, fluticasone propionate, prednisolone, methylprednisolone 6-alpha, hydrocortisone base, fluorometholone, finasteride, fluocinonide and cortisol acetate.

In addition, the present invention provides a health functional food composition for improving lung cancer comprising: at least a glucocorticoid-based compound selected from the group consisting of clobetasol propionate, amcinonide, betamethasone valerate, hydrocortisone valerate, flunisolide, flurandrenolide, flumethasone, desonide, beclomethasone dipropionate, triamcinolone acetonide, budesonide, mometasone furoate, desoxymetasone, clocortolone pivalate, prednisolone hemisuccinate, hydrocortisone butyrate, betamethasone sodium phosphate, hydrocortisone, diflorasone diacetate, prednisolone sodium phosphate, prednicarbate, triamcinolone, methylprednisolone sodium succinate, triamcinolone diacetate, rimexolone, isoflupredone acetate, betamethasone, dexamethasone acetate, melengestrol acetate, fluticasone propionate, prednisolone, methylprednisolone 6-alpha, hydrocortisone base, fluorometholone, finasteride, fluocinonide and cortisol acetate; and a mTOR inhibitor.

Furthermore, the present invention provides a health functional food composition for improving lung cancer comprising: at least a glucocorticoid-based compound selected from the group consisting of clobetasol propionate, amcinonide, betamethasone valerate, hydrocortisone valerate, flunisolide, flurandrenolide, flumethasone, desonide, beclomethasone dipropionate, triamcinolone acetonide, budesonide, mometasone furoate, desoxymetasone, clocortolone pivalate, prednisolone hemisuccinate, hydrocortisone butyrate, betamethasone sodium phosphate, hydrocortisone, diflorasone diacetate, prednisolone sodium phosphate, prednicarbate, triamcinolone, methylprednisolone sodium succinate, triamcinolone diacetate, rimexolone, isoflupredone acetate, betamethasone, dexamethasone acetate, melengestrol acetate, fluticasone propionate, prednisolone, methylprednisolone 6-alpha, hydrocortisone base, fluorometholone, finasteride, fluocinonide and cortisol acetate; and an AMPK inhibitor.

Advantageous Effects

According to the present invention, a glucocorticoid-based compound selected from the group consisting of clobetasol propionate, amcinonide, betamethasone valerate, hydrocortisone valerate, flunisolide, flurandrenolide, flumethasone, desonide, beclomethasone dipropionate, triamcinolone acetonide, budesonide, mometasone furoate, desoxymetasone, clocortolone pivalate, prednisolone hemisuccinate, hydrocortisone butyrate, betamethasone sodium phosphate, hydrocortisone, diflorasone diacetate, prednisolone sodium phosphate, prednicarbate, triamcinolone, methylprednisolone sodium succinate, triamcinolone diacetate, rimexolone, isoflupredone acetate, betamethasone, dexamethasone acetate, melengestrol acetate, fluticasone propionate, prednisolone, methylprednisolone 6-alpha, hydrocortisone base, fluorometholone, finasteride, fluocinonide and cortisol acetate, inhibits cell growth by inhibiting NRF2 in KEAP1 mutant lung cancer or KEAP1 and LKB1 mutant lung cancer and has a more strong anticancer effect in combination with mTOR inhibitor, thereby being useful for the treatment or improvement of lung cancer including KEAP1 mutation.

In addition, in KEAP1 and LKB1 normal lung cancer, it is confirmed that an nutrient deficient state, one of the characteristics of the tumor microenvironment activates NRF2 and also does AMPK by LKB1 and in this lung cancer, glucocorticoid-based compounds in combination with AMPK inhibitor exhibit synergistic effect against cancer and thus can be useful for the treatment or improvement of KEAP1 normal lung cancer.

DESCRIPTION OF DRAWINGS

FIGS. 2a-2b and 3a-3b show screening results for NRF2-inhibiting compounds in the KEAP1 mutant lung cancer cell line using 1887 clinical compound library.

FIGS. 4a-4f and 5a-5h show the mechanism of NRF2 inhibition by clobetasol propionate which is the most effective of glucocorticoids (GCs)-based drugs in the KEAP1-mutant lung cancer cell line.

FIGS. 6a-6d show the inhibitory effect of clobetasol propionate on the expression of NRF2 target in KEAP1 mutant cell line and the effect of increasing active oxygen thereby.

BEST MODE

Figure 1A:
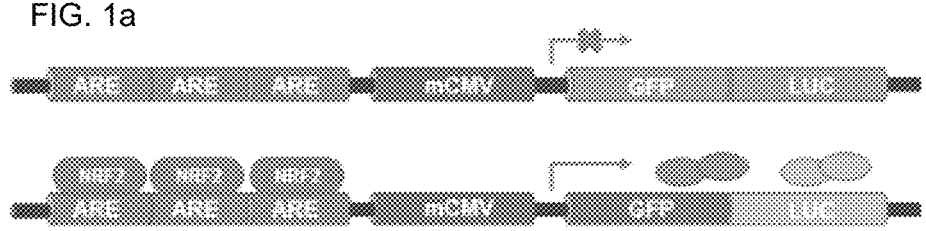
FIGS. 1a-1d show the verification for the accuracy and the validity of the luciferase activity assay system for NRF2 inhibitor screening.

Inventors of the present invention has established anticancer strategy that mTOR (mechanistic target of rapamycin) and NRF2 (Nuclear factor (erythroid-derived 2)-like 2) known as signal transfer targets activated by LKB1/KEAP1 mutations, are inhibited at the same time, based on the report of our previous studies (not published) and the prior known studies (J Thorac Oncol, 2014, June; 9 (6): 794-804; Cancer Discov, 2015, 860-77) in which KEAP1 (kelch-like ECH-associated protein 1) and LKB1 (liver kinase B1) were often found to be mutated together in the assay of the gene combination mutated in the actual lung cancer. In addition, they also has established anticancer strategy for inhibiting NRF2 and AMPK together by confirming that an nutrient deficient state, one of the characteristics of the tumor microenvironment activates NRF2 and also does AMPK (AMP-activated protein kinase) by LKB1 in KEAP1/LKB1 normal lung cancer.

For this purpose, we screened NRF2-inhibiting drugs among 1887 clinical compound libraries provided by Korea Compound Bank and identified 13 glucocorticoid-based compounds having at least 50% inhibitory effect and the anticancer effect is confirmed by the most effective clobetasol propionate among them. Firstly, it is confirmed that the cell growth inhibitory effect on KEAP1 mutation lung cancer cells and in particular, the combination of clobetasol propionate and rapamycin, an mTOR inhibitor, showed anticancer synergy effect in lung cancer cells in which KEAP1/LKB1 are mutated together. In addition, KEAP1/LKB1 gene normal lung cancer cell line cultured in clobetasol propionate and AMPK inhibitor sunitinib under low nutrient conditions is confirmed to have anticancer synergistic effects.

The KEAP1 is present in the E3 ubiquitin ligase complex and inhibits its function by inducing degradation by binding to the NRF2 protein, a transcription factor. If the KEAP1 gene is mutated in cancer cells (20-30% in lung cancer), the amount of NRF2 protein is increased to increase the transcription of the target gene, thereby increasing the activity of antioxidant enzymes, which is a target of NRF2.

The LKB1 is a STK11 (Serine/Threonine Kinase 11), and is also known as a tumor suppressor gene that is frequently mutated or suppressed in lung cancer (20~30%) and uterine cancer and colorectal cancer. 12 types of substrate of LKB1 are presently known and the mTORC1 inhibitory signal transduction pathway by the activation of AMPK is disclosed to have the tumor inhibitory function of LKB1. However, the activation of AMPK by LKB1 plays a very important role in maintaining the energy homeostasis of cells, which is a tumor promoting function because it is very important for the survival of cancer cells in the nutrient deficient tumor microenvironment. Therefore, the LKB1-AMPK pathway is known to perform both tumor-inhibiting and tumor-promoting functions depending on the situation.

Accordingly, the present invention provides a pharmaceutical composition for treating lung cancer comprising at least a glucocorticoid-based compound selected from the group consisting of clobetasol propionate, amcinonide, betamethasone valerate, hydrocortisone valerate, flunisolide, flurandrenolide, flumethasone, desonide, beclomethasone dipropionate, triamcinolone acetonide, budesonide, mometasone furoate, desoxymetasone, clocortolone pivalate, prednisolone hemisuccinate, hydrocortisone butyrate, betamethasone sodium phosphate, hydrocortisone, diflorasone diacetate, prednisolone sodium phosphate, prednicarbate, triamcinolone, methylprednisolone sodium succinate, triamcinolone diacetate, rimexolone, isoflupredone acetate, betamethasone, dexamethasone acetate, melengestrol acetate, fluticasone propionate, prednisolone, methylprednisolone 6-alpha, hydrocortisone base, fluorometholone, finasteride, fluocinonide and cortisol acetate.

The lung cancer may be KEAP1 mutant lung cancer or KEAP1 and LKB1 mutant lung cancer.

Also, the lung cancer may be non-small cell lung cancer.

In addition, the pharmaceutical composition according to the present invention may further comprise an inhibitor of mTOR which is a target activated by mutated KEAP1/LKB1 signal transfer.

Accordingly, the present invention provides a pharmaceutical composition for treating lung cancer comprising: at least a glucocorticoid-based compound selected from the group consisting of clobetasol propionate, amcinonide, betamethasone valerate, hydrocortisone valerate, flunisolide, flurandrenolide, flumethasone, desonide, beclomethasone dipropionate, triamcinolone acetonide, budesonide, mometasone furoate, desoxymetasone, clocortolone pivalate, prednisolone hemisuccinate, hydrocortisone butyrate, betamethasone sodium phosphate, hydrocortisone, diflorasone diacetate, prednisolone sodium phosphate, prednicarbate, triamcinolone, methylprednisolone sodium succinate, triamcinolone diacetate, rimexolone, isoflupredone acetate, betamethasone, dexamethasone acetate, melengestrol acetate, fluticasone propionate, prednisolone, methylprednisolone 6-alpha, hydrocortisone base, fluorometholone, finasteride, fluocinonide and cortisol acetate; and a mTOR inhibitor.

The mTOR inhibitor is at least one selected from the group consisting of rapamycin, temsirolimus, everolimus, ridaforolimus, AZD-8055, AZD-2014, OSI-027, INK128, PP242, NVP-BEZ235, XL765, BGT226 and PF-04691502, and more preferably, it may be rapamycin, but it is not limited thereto.

In addition, the lung cancer may also be KEAP1 mutant lung cancer or KEAP1 and LKB1 mutant lung cancer.

Moreover, the lung cancer may be non-small cell lung cancer.

The pharmaceutical composition may comprise 1 to 50 weight % of the glucocorticoid-based compound and 50 to 99 weight % of the mTOR inhibitor, and it is preferable that NRF2 and mTOR are most effectively inhibited within this range to exhibit a therapeutic effect of lung cancer.

Furthermore, the pharmaceutical composition of the present invention may further comprise an inhibitor of AMPK which is a target activated in the signal transfer of KEAP1/LKB1 normal lung cancer cells.

Namely, the present invention provides a pharmaceutical composition for treating lung cancer comprising: at least a glucocorticoid-based compound selected from the group consisting of clobetasol propionate, amcinonide, betamethasone valerate, hydrocortisone valerate, flunisolide, flurandrenolide, flumethasone, desonide, beclomethasone dipropionate, triamcinolone acetonide, budesonide, mometasone furoate, desoxymetasone, clocortolone pivalate, prednisolone hemisuccinate, hydrocortisone butyrate, betamethasone sodium phosphate, hydrocortisone, diflorasone diacetate, prednisolone sodium phosphate, prednicarbate, triamcinolone, methylprednisolone sodium succinate, triamcinolone diacetate, rimexolone, isoflupredone acetate, betamethasone, dexamethasone acetate, melengestrol acetate, fluticasone propionate, prednisolone, methylprednisolone 6-alpha, hydrocortisone base, fluorometholone, finasteride, fluocinonide and cortisol acetate; and an AMPK inhibitor.

At this time, the AMPK inhibitor may be at least one selected from the group consisting of sunitinib and dorsomorphin (compound C), more preferably sunitinib, but it is not limited thereto.

The lung cancer may be KEAP1 and LKB1 normal lung cancer, and the pharmaceutical composition according to the present invention may exhibit the most excellent therapeutic effect in such lung cancer.

The lung cancer also may be non-small cell lung cancer.

Meanwhile, the pharmaceutical composition may contain 1 to 50 weight % of a glucocorticoid-based compound and 50 to 99 weight % of an AMPK inhibitor, and it is preferable because it can exhibit the therapeutic effect of lung cancer by inhibiting AMPK most effectively within this range.

The pharmaceutical composition may further comprise an appropriate carrier, excipient or diluent conventionally used in the production of a pharmaceutical composition, in addition to the glucocorticoid-based compound, the mTOR inhibitor and the AMPK inhibitor.

Examples of carriers, excipients or diluents which can be used in the present invention include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate or mineral oil, etc.

The pharmaceutical composition according to the present invention may be formulated in the form of oral preparations such as powders, granules, tablets, capsules, suspensions, emulsions, syrups, aerosols or the like, externals, suppositories and sterilized injection solutions according to a conventional method.

In the case of formulation, a diluent or excipient such as a filler, an extender, a binder, a wetting agent, a disintegrant, a surfactant or the like is used. Solid formulations for oral administration include tablets, pills, powders, granules, capsules and the like, which may contain at least one excipient such as starch, calcium carbonate, sucrose, lactose, gelatin and the like.

In addition to simple excipients, lubricants such as magnesium stearate and talc are also used. Liquid preparations for oral administration include suspensions, solutions, emulsions, and syrups. Various excipients such as wetting agents, sweetening agents, fragrances, preservatives, etc. may be included in addition to water and liquid paraffin which are commonly used simple diluents.

Formulations for parenteral administration include sterile aqueous solutions, non-aqueous solutions, suspensions, emulsions, freeze-dried preparations, and suppositories. Examples of the suspending agent, non-aqueous solution include propylene glycol, polyethylene glycol, vegetable oil such as olive oil, injectable ester such as ethyl oleate, etc. As the base of suppositories, witepsol, macrogol, tween 61, cacao butter, laurinum, glycerogelatin, etc. can be used.

In addition, the mixed amount of the glucocorticoid-based compound or the mTOR inhibitor used as the active ingredient of the pharmaceutical composition of the present invention may vary depending on the age, sex, body weight and disease of the patient, but is 0.001 to 100 mg/kg, preferably 0.01 to 10 mg/kg and can be administered once to several times a day.

Further, the dosage of the pharmaceutical composition according to the present invention may be increased or decreased depending on the route of administration, degree of disease, sex, weight, age and the like. Accordingly, the dosage amounts do not limit the scope of the invention in any manner.

The pharmaceutical composition may be administered to mammals such as rats, mice, livestock, humans, and the like in a variety of routes. All modes of administration may be expected, for example, by oral, rectal or intravenous, intramuscular, subcutaneous, intratracheal, intrauterine or intracerebroventricular injections.

Furthermore, the present invention provides a health functional food composition for improving lung cancer comprising at least a glucocorticoid-based to compound selected from the group consisting of clobetasol propionate, amcinonide, betamethasone valerate, hydrocortisone valerate, flunisolide, flurandrenolide, flumethasone, desonide, beclomethasone dipropionate, triamcinolone acetonide, budesonide, mometasone furoate, desoxymetasone, clocortolone pivalate, prednisolone hemisuccinate, hydrocortisone butyrate, betamethasone sodium phosphate, hydrocortisone, diflorasone diacetate, prednisolone sodium phosphate, prednicarbate, triamcinolone, methylprednisolone sodium succinate, triamcinolone diacetate, rimexolone, isoflupredone acetate, betamethasone, dexamethasone acetate, melengestrol acetate, fluticasone propionate, prednisolone, methylprednisolone 6-alpha, hydrocortisone base, fluorometholone, finasteride, fluocinonide and cortisol acetate.

In addition, the present invention provides a health functional food composition for improving lung cancer comprising: at least a glucocorticoid-based compound selected from the group consisting of clobetasol propionate, amcinonide, betamethasone valerate, hydrocortisone valerate, flunisolide, flurandrenolide, flumethasone, desonide, beclomethasone dipropionate, triamcinolone acetonide, budesonide, mometasone furoate, desoxymetasone, clocortolone pivalate, prednisolone hemisuccinate, hydrocortisone butyrate, betamethasone sodium phosphate, hydrocortisone, diflorasone diacetate, prednisolone sodium phosphate, prednicarbate, triamcinolone, methylprednisolone sodium succinate, triamcinolone diacetate, rimexolone, isoflupredone acetate, betamethasone, dexamethasone acetate, melengestrol acetate, fluticasone propionate, prednisolone, methylprednisolone 6-alpha, hydrocortisone base, fluorometholone, finasteride, fluocinonide and cortisol acetate; and a mTOR inhibitor.

The mTOR inhibitor is at least one selected from the group consisting of rapamycin, temsirolimus, everolimus, ridaforolimus, AZD-8055, AZD-2014, OSI-027, INK128, PP242, NVP-BEZ235, XL765, BGT226 and PF-04691502, and more preferably, it may be rapamycin, but it is not limited thereto.

Also, the present invention provides a health functional food composition for improving lung cancer comprising: at least a glucocorticoid-based compound selected from the group consisting of clobetasol propionate, amcinonide, betamethasone valerate, hydrocortisone valerate, flunisolide, flurandrenolide, flumethasone, desonide, beclomethasone dipropionate, triamcinolone acetonide, budesonide, mometasone furoate, desoxymetasone, clocortolone pivalate, prednisolone hemisuccinate, hydrocortisone butyrate, betamethasone sodium phosphate, hydrocortisone, diflorasone diacetate, prednisolone sodium phosphate, prednicarbate, triamcinolone, methylprednisolone sodium succinate, triamcinolone diacetate, rimexolone, isoflupredone acetate, betamethasone, dexamethasone acetate, melengestrol acetate, fluticasone propionate, prednisolone, methylprednisolone 6-alpha, hydrocortisone base, fluorometholone, finasteride, fluocinonide and cortisol acetate; and an AMPK inhibitor.

At this time, the AMPK inhibitor may be at least one selected from the group consisting of sunitinib and dorsomorphin (compound C), more preferably sunitinib, but it is not limited thereto.

The health functional food may be provided in the form of powder, granules, tablets, capsules, syrups or beverages. The health functional food may be mixed with other food or food additives in addition to the active ingredient of a glucocorticoid-based compound, an mTOR inhibitor or an AMPK inhibitor and can be suitably used according to a conventional method. The amount of the active ingredient to be mixed can be suitably determined according to its use purpose such as health or to therapeutic treatment.

The effective dose of the glucocorticoid-based compound, mixture of the mTOR inhibitor and the same or a mixture of the AMPK inhibitor and the same contained in the health functional food may be used in accordance with the effective dose of the pharmaceutical composition, but in case of the purpose of health and hygiene or long intake for health. It may be less than the above range and since the active ingredient has no problem in terms of safety, it can be used in an amount of more than the above range.

There is no particular limitation on the kind of the health functional food, and examples thereof include meat, sausage, bread, chocolate, candy, snack, confectionery, pizza, ramen and other noodles, gums, dairy products including ice cream, various soups, a drink, an alcoholic beverage and a vitamin complex, etc.

Hereinafter, examples of the present invention will be described in detail to understand the present invention. The present invention may, however, be embodied in many different forms and should not be limited to the embodiments set forth herein in order to clearly illustrate the present invention for those skilled in the art to which the present invention pertains.

Preparation Example 1

For the experiments, H1299 (KEAP1-normal, LKB1-normal) which is normal non-small cell lung carcinoma cell line (NSCLC) and KEAP1 mutant non-small cell lung cancer cell lines (H2228 (KEAP1-mutant, LKB1-normal), A549 (KEAP1-mutant, LKB1-mutant), H460 (KEAP1-mutant and LKB1-mutant)) were purchased from the Korean Cell Line Bank and cultured in Dulbecco's modification of Eagle's Medium (DMEM, HyClone Laboratories, USA) supplemented with 10% fetal bovine serum (FBS, Invitrogen), 1% penicillin-streptomycin and 1% HEPES, at 5% $CO_2$ and 37'C. In subsequent experiments, A549-ARE cells were seeded at high density in 96-well plates for screening and treated with the 1887 clinical compound library (Korean Chemical Bank). Clobetasol propionate (CP) was purchased from Sigma-Aldrich (St. Louis, USA). In addition, the others necessary for the experiment were purchased from Sigma (CT99021, GSK3 inhibitor), EMD Millipore (MG132), LC laboratories (Rapamycin), and antibodies used for Western blot analysis were GeneTex (ME1, IDH1, G6PD, PGD, GCLM, GCR, NRF2), Cell Signaling Technology (NRF2, LKB1, p-AMPK, AMPK, pGSK-3, GSK3, p-p70S6K, p70S6K, α-tubulin), Sigma (KEAP1) and Proteintech (SRXN1).

<Example 1> NRF2 Inhibitor Screening (1) Establishment of ARE-Luciferase Cell Line for Measuring NRF2 Activity In order to screen for an effective NRF2 inhibitor, as shown in FIG. 1a, luciferase/green fluorescent protein (GFP) dual antioxidant responsive element (ARE)-DNA base sequence (CACCGTGACTCAGCAATTx3) system was established in A549 (LKB1 normal/KEAP1 mutant) non-small cell lung cancer cells having high NRF2 activity.

To demonstrate that the highly active luciferase and GFP signals in A549 cell lines are specific for NRF2 activity, three doxycyclin-inducible NRF2-shRNAs with different sequences as shown in the Table 1 below were prepared. In order to construct a Tet-inducible shRNA expression system, the following shRNAs were inserted into a tet-pLKO-pyro vector (Dmitri Wiederschain: Addgene plasmid #21915) and then A549-ARE cell line expressing doxycycline-inducible NRF2-shRNA was established by the transduction.

Then, 0.2 µg/mL of doxycycline (DOX; Clontech) was treated every 2 days in the medium to induce NRF2-shRNA expression. Thereafter, the NRF2 expression inhibition efficiency was verified by Western blotting, luciferase activity measurement and GFP expression measurement using a fluorescence microscope.

TABLE 1

| shRNA | Sequence | SEQ. NO. |
|---|---|---|
| NRF2sh-1 | CCGGAGTTGAGCTTCATTGAACTGCCTCGA GGCAGTTCAATGAAGCTCAACTTTTTG | 1 |
| NRF2sh-2 | CCGGGCTCCTACTGTGATGTGAAATCTCGA GATTTCACATCACAGTAGGAGCTTTTTG | 2 |
| NRF2sh-3 | CCGGAGAGCAAGATTTAGATCATTTCTCGA GAAATGATCTAAATCTTGCTCTTTTTG | 3 |

Specifically, for Western blotting, the A549 cells expressing Tet-pLKO-NCshRNA (negative control) and three Tet-pLKO-NRF2 shRNAs were treated with doxycycline for 3 days and 6 days, followed by separation of proteins. Each separated 10 µg of the protein was loaded on 8% acrylamide gel, electrophoresed, transferred to nitrocellulose (NC) membrane, and NRF2 antibody (Cell signaling, 1:1000) and actin antibody (SCBT, 1:1000) were diluted in TBST (Tris-Buffered Saline with Tween 20) buffer containing 5% skim milk and reacted overnight at 4° C. Subsequently, the secondary antibody was reacted for 1 hour, washed with TBST, and the protein expression level was measured using ECL (Enhanced chemiluminescence).

In addition, A549-ARE cells were firstly dispensed into $5 \times 10^3$ cells per well in a 96 well plate, and each of the clinical compounds was treated with various concentrations (1 μM or 5 μM) after 24 hours. After 24 hours, 30 μl of a lysis buffer was added, and the mixture was dissolved at 4° C. for 40 minutes using a rocker. 20 μl of the dissolved product was added to a 96-well white plate and 100 μl of a luciferase substrate buffer having the following composition was added thereto and luciferase activity was measured by using a plate reader.

Buffer for Substrate
1. Buffer A
1 mM D-Luciferin, pH 6.1-6.4 (yellow light), stored at −20° C.
2. Buffer B
40 mM Tricin (MW 179.2)
2.14 mM $(MgCO_3)_4Mg(OH)_2 \cdot 5H_2O$ (MW 485.7)
5.34 mM $MgSO_4 \cdot 7H2O$ (MW 246.48)
66.6 mM dithiothreitol (DTT, MW 1542)
1.06 mM adenosine triphosphate (ATP, MW 551)
0.54 mM Coenzyme (MW 767.5)
0.2 mM ethylenediaminetetraacetic acid (EDTA, Stock 0.5M EDTA, pH 7.8, stored at ~20° C.)
3. Make a Assay Mixture (1:1)=substrate buffer
Lysis Buffer
0.1 M potassium phosphate buffer, pH 7.8
(1M $K_2HPO_4$, 1M $KH_2PO_4$)
1% Triton X-100
1 mM DTT
2 mM EDTA The remaining dissolved product was diluted five times with distilled water (DW) and the protein concentration was measured by the Bradford assay (BioRad). Specifically, 200 μl of the Bradford reagent (Coomassie Brilliant Blue G-250) diluted times with distilled water was reacted with 5 μl of the remaining dissolved product and absorbance was measured at 595 nM. The protein concentration of the dissolved products was calculated by the same experiment using BSA solution as a standard protein. The luciferase value was calibrated by dividing the luciferase value measured above by the measured protein concentration.

Figure 1B:
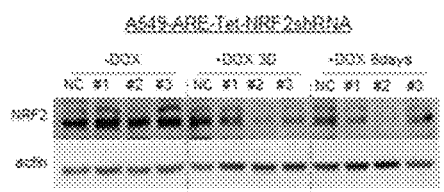
Figure 1C:
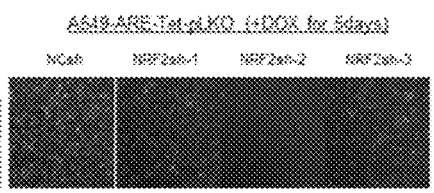
Figure 1D:
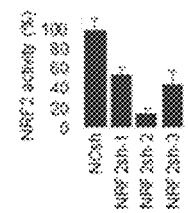

As a result, NRF2sh-2 inhibited NRF2 protein expression, luciferase activity and GFP signal most effectively, as shown in FIGS. 1b, 1c and 1d and it indicates that it is specific for the luciferase activity and GFP signal, which are highly expressed in A549.

(2) Screening Using 1887 Clinical Compound Library

As shown in FIG. 2a, NRF2 inhibitory compounds were screened among the 1887 kinds of clinical compound libraries provided by Korean Chemical Bank using the above luciferase/GFP dual ARE-receptor cell line system. Namely, the luciferase assays were performed using A438-ARE cells as the method of the Example 1.

As a result, as shown in FIG. 2b, glucocorticoids (GCs)-based drugs among clinical compounds showed NRF2 inhibitory effect and most of the GCs-based drugs have inhibitory effect of at least 50% by treatment with 1 μM concentration for 24 hours.

(3) NRF2 Inhibitory Effect of Glucocorticoids-Based Drugs

From the results obtained above, 13 kinds of GCs-based drugs having excellent effects were selected and the NRF2 inhibitory effect was compared according to the concentration of 13 kinds of GCs-based drugs by carrying out the above luciferase assay.

Figures 3A, 3B:
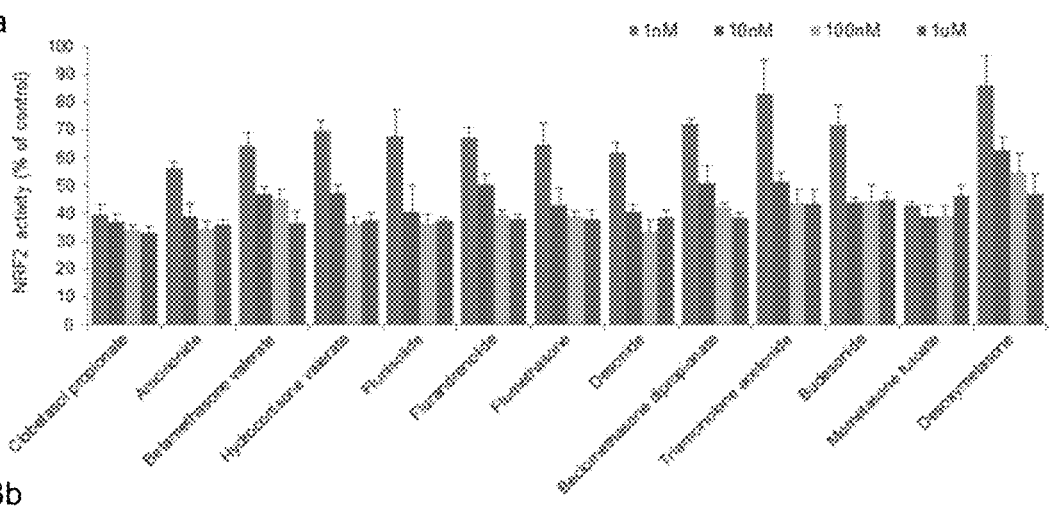

As a result, as shown in FIGS. 3a and 3b, most has excellent inhibitory effects from 10 nM level and in particular, clobetasol propionate showed excellent effect from 1 nM and showed the most excellent inhibitory effect even at 1 μM.

<Example 2> Confirmation of NRF2 Inhibition Mechanism by Clobetasol Propionate (1) Confirmation of Mechanism of Clobetasol Propionate Glucocorticoids act as ligands for a nuclear receptor subfamily 3 (group C, member 1), known as the glucocorticoid receptor (GC receptor, GCR). When glucocorticoids bind to GCR, GCR induces transcriptional promotion or transcriptional inhibition of many genes involved in various functions in vivo such as inflammation or metabolism. Based on the known facts, GCR-shRNA was used to inhibit GCR expression in order to confirm the relationship of NRF2 inhibitory effect of glucocorticoid, i.e. clobetasol propionate, to GCR, and then the Western blot and luciferase assay.

Firstly, the A549-tet-on cells transfected with the vector containing GCR-shRNA were constructed and after the treatment with doxycycline and clobetasol propionate, and protein extracts were prepared by hemolysis with cell lysis buffer (Cell signaling technology) supplemented with protease inhibitor cocktail (EMD millipore) to perform Western blotting. Then, western blotting was carried out in the same manner as in the Example 1. At this time, the concentration of the protein was determined by performing a Bradford assay according to the Example 1. In addition, luciferase assays were carried out in the same manner as in the Example 1.

Figure 4A:
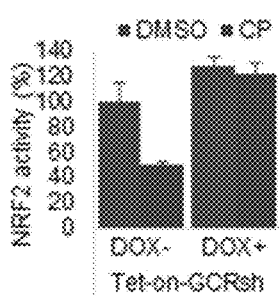
Figure 4B:
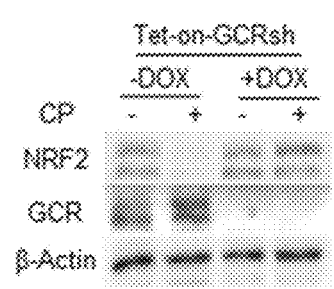

As a result, as shown in FIGS. 4a and 4b, GCR expression inhibition completely prevented NRF2 inhibition by clobetasol propionate. That is, clobetasol propionate significantly reduced the level and activity of the NRF2 protein, which was blocked by the inhibition of GCR expression. Namely, it clearly shows that the NRF2 inhibitory effect of clobetasol propionate, I.e. glucocorticoid, is related to GCR.

(2) Effect of Clobetasol Propionate According to Concentrations

In order to clearly confirm the effect of clobetasol propionate according to concentrations, the activity of NRF2 was measured by performing luciferase assays as described in the Example 1 on cells treated with 100 nM or 1 μM of clobetasol propionate for 8, 24 and 48 hours.

Figure 4C:
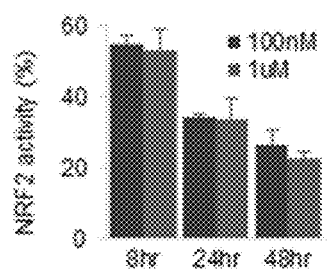
Figure 4D:
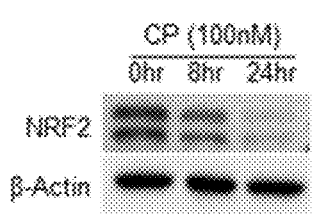

As a result, as shown in FIGS. 4c and 4d, the inhibition of NRF2 activity by clobetasol propionate was maintained at a concentration of 100 nM for at least 48 hours, and this result was consistent with the decreased amount of NRF2 protein. This means that glucocorticoids inhibit NRF2 by decreasing its protein expression.

(3) Measurement of Effect on NRF2 mRNA and Protein Degradation

According to accumulated research results, NRF2 protein levels can be regulated by mRNA transcription, or proteasome related degradation. To confirm whether NRF2 is suppressed through mRNA transcription inhibition or NRF2 is suppressed by promoting proteasome-related degradation, real-time PCR was performed on the cells, and MG132, a proteasome inhibitor, was treated and Western blotting was performed in the same manner as in the Example 1.

Specifically, for real-time PCR, total RNA was extracted from A549 cells using TRIZol (Invitrogen). Then, 1 μg of total RNA was reverse transcribed to cDNA using oligo dT primer and SuperScript II Reverse Transcriptase according to the manufacturer's instructions (Invitrogen). Thereafter, PCR was performed according to the manufacturer's instructions (Affymetrix) using HotStart-IT SYBR Green qPCR Master Mix. Primers of NRF2 and β-actin used in the PCR were as shown in Table 2 below.

TABLE 2

| Gene | Forward/Reverse | Sequence | SEQ. No. |
|---|---|---|---|
| NRF2 | Forward | CGGTATGCAACAGGACATTG | 4 |
|  | Reverse | ACTGGTTGGGGTCTTCTGTG | 5 |
| β-actin | Forward | TGCCATCCTAAAAGCCAC | 6 |
|  | Reverse | TCAACTGGTCTCAAGTCAGTG | 7 |

Figure 4E:
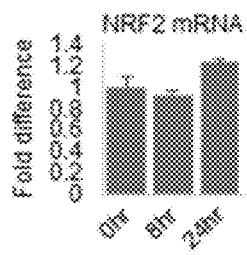
Figure 4F:
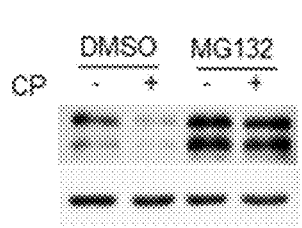

As a result, as shown in FIGS. 4e to 4f, clobetasol propionate did not affect the mRNA level of NRF2 itself, however in contrast with the above, when MG132 was treated, the amount of NRF2 protein inhibited by clobetasol propionate was recovered. Based on this result, it was confirmed that the clobetasol propionate compound induced GCR-dependent proteasome-related degradation thereby inhibiting NRF2.

(4) Confirmation of NRF2 Protein Degradation Mechanism

In general, proteasome degradation of the NRF2 protein consists of two pathways as shown in FIG. 5a: i.e. a pathway by KEAP1 and a pathway by GSK3-β-TrCP. Based on the results, GSK3 inhibitor and clobetasol propionate were administered to the KEAP1 mutant A549 cells prepared in the Preparation Example and the luciferase assay and Western blotting was performed as the Example 1, to determine whether NRF2 is inhibited by regulating glucocorticoid compound through which of the two pathways. In addition, A549-tet-on cells transfected using a vector containing the β-TrCP shRNA, were established and Western blotting and luciferase assay were performed for cells in which β-TrCP gene was knocked down with the doxycycline.

As a result, as shown in FIGS. 5b and 5c, NRF2 proteolysis and inhibition of activity of NRF2 induced by clobetasol propionate was inhibited by GSK3 inhibitor treatment. In addition, as shown in FIG. 5d, when β-TrCP was knocked down, it also inhibited proteolysis of NRF2 induced by clobetasol propionate. That is, this result means that the glucocorticoid compound degrades the NRF2 protein using the pathway through GSK3-p-TrCP.

Furthermore, GSK3 inhibits the migration of NRF2 to the nucleus, as known so far. To prove this, cells treated with GSK3 inhibitor and clobetasol propionate under the treatment of MG132 were divided into nuclei and cytoplasm and then subjected to Western blotting.

Figure 5E:
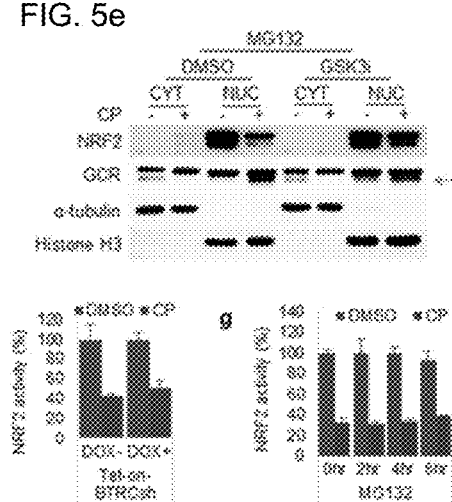

As a result, as shown in FIG. 5e, the migration of NRF2 into the nucleus was inhibited by the treatment with clobetasol propionate, and this effect was completely blocked by the GSK3 inhibitor. This result supports that inhibition of NRF2 protein degradation by MG132 treatment or β-TrCP knock-down does not recover the inhibition of NRF2 activity by glucocorticoids, as shown in FIGS. 5f and 5g. That is, the glucocorticoid compound not only degrades NRF2 by activating GSK3, but also inhibits NRF2 by inhibiting the migration of NRF2 to the nucleus.

Accordingly, as shown in FIG. 5h, these results indicate that glucocorticoids inhibit NRF2 by the inhibition of NRF2 migration into the nucleus and GSK3 activation which promotes β-TrCP-dependent degradation.

<Example 3> Inhibition of NRF2 Target Protein Expression and Increase in Active Oxygen by Clobetasol Propionate (1) Measurement of NRF2 Expression Level in Lung Cancer Cell Line In general, NRF2 is highly expressed in KEAP1 mutant cells, and p-AMPK is known to be low in LKB1 mutant cells. To confirm this, Western blotting was performed on the 4 cells. Specifically, to verify the presence of KEAP1 and LKB1 mutations in KEAP1 mutant cells H2228 (KEAP1-mutant, LKB1-normal), A549 (KEAP1-mutant, LKB1-mutant), H460 (KEAP1-mutant, LKB1-mutant), and normal gene cells H1299 (KEAP1-normal, LKB1-normal), Western blot analysis was carried out in the same manner as in the Example 1 to confirm NRF2 and p-AMPK expression levels.

As a result, as shown in FIG. 6a, the NRF2 expression level was high in the H2228, A549, and H460 cell lines and thus, it was confirmed that the KEAP1 mutation was occurred and the A549 and H460 cell lines had the LKB1 mutation from the low activity of AMPK.

(2) Confirming the Effect of Clobetasol Propionate

In order to confirm the effect of glucocorticoid on cells having high NRF2-activity, KEAP1 mutant cells (A549 and H2228) were treated with clobetasol propionate for 2 days, 4 days or 5 days, the expression of major NRF2 target proteins (G6PD, PGD, ME1, GCLM, AKR1B10 and AKR1C3) associated with redox regulation was measured by the Western blotting. As a control, the cell was used, in which NRF2-shRNA was transformed to H2228 cell line to inhibit NRF2 expression.

As a result, as shown in FIG. 6b, it was confirmed that both the control in which NRF2-shRNA is transformed to H2228 cell line and the cell that clobetasol propionate is treated effectively inhibited expression of NRF2 target which has antioxidative activity. Likewise, as shown in FIG. 6c, when the A549 cell line was treated with clobetasol propionate, NRF2 target protein expression was also effectively inhibited.

In addition, because ME1 and GCLM proteins have detoxification activity of hydrogen peroxide, to confirm this change, the amount of hydrogen peroxide after the treatment with clobetasol propionate was measured as follows: The A549 and H2228 cell lines were cultured in 5 μM CMH2DCF-DA (Invitrogen) after the incubation for 30 minutes, the cultured cells were washed twice with phosphate buffered saline and incubated in the dark for 40 minutes with 90% dimethylsulfoxide (DMSO) and 10% PBS, and the fluorescent dye was released. After the culture, the supernatant of the culture liquid was dispensed into a 96-well plate and the amount of fluorescence was measured at 480/530 nm. For standardization of the measured fluorescence intensity, the cells remaining after removing the supernatant and washing with PBS, were stained with a crystal violet solution (20% methanol and 0.5% crystal violet) for 10 minutes at room temperature. After washing three times, the incubation was performed for solubilization in 1% SDS solution and absorbance at 570 nm was measured.

As a result, as shown in FIG. 6d, it was confirmed that when A549 and H2228 were treated with clobetasol propionate, active oxygen was significantly increased. Namely, it proves that glucocorticoids such as clobetasol propionate can effectively inhibit the antioxidant function of NRF2.

<Example 4> Anticancer Effect of Clobetasol Propionate Sole and Synergistic Effect of Combined Use with Rapamycin (1) In Vitro Experiments The synergistic anticancer effects of the treatment of clobetasol propionate sole and the combined use with rapamycin, an mTOR inhibitor on LKB1/KEAP1 normal lung cancer cell line H1299, KEAP1 mutant cell line H2228, LKB1/KEAP1 mutant lung cancer cell lines A549 and H460 were analyzed by soft agar assay. In order to confirm whether the tumor inhibitory effect of clobetasol propionate was due to NRF2 inhibition, the effect was compared with tumor suppression effect in NRF2 knock-down lung cancer cell line using NRF2-shRNA-2, which was used in the Example 2.

Specifically, 50 µl of a 0.7% agar-containing DMEM medium was added into a 12-well plate and was solidified (bottom agar) and 300 µl of a DMEM medium containing $3 \times 10^3$ cells and 0.35% agar was placed on the solidified agar medium and solidified (top agar+/− Doxycycline). After solidification, 250 µl of DMEM medium (+/− Doxycycline) was added and the number of colonies formed after culturing for 2 weeks in a $CO_2$ incubator was determined, and the result was shown in FIGS. 7a to 7e.

Figure 7A:
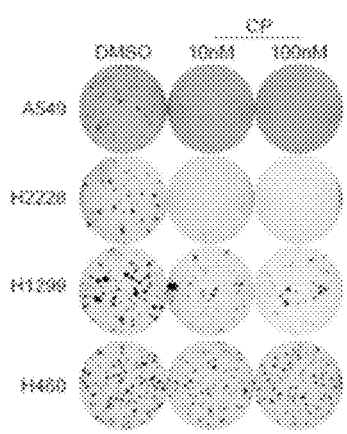
FIGS. 7a-7e and 8a-8d show the in vitro and in vivo anticancer synergistic effects of clobetasol propionate alone and in combination with mTOR inhibitor rapamycin in KEAP1-mutant or KEAP1-mutant/LKB1-mutant lung cancer cell lines.
Figure 7B:
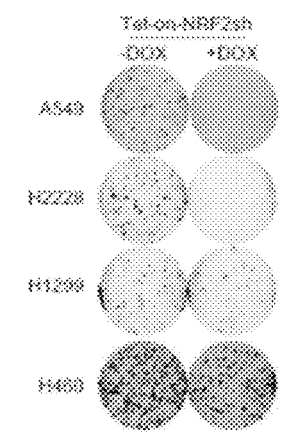

As a result, as shown in FIGS. 7a and 7b, the KEAP1 mutant cell lines A549 and H2228 were strongly inhibited by the clobetasol propionate treatment and the NRF2 knock-down, but in the KEAP1 normal cell line H1299, the clobetasol propionate treatment and the NRF2 knock-down did not significantly affect the cell growth. This result shows that the anticancer effect of glucocorticoids depends on the inhibition of NRF2.

(2) Effect of Clobetasol Propionate and Rapamycin on LKB1 Mutant Cell Line H460

Figure 7C:
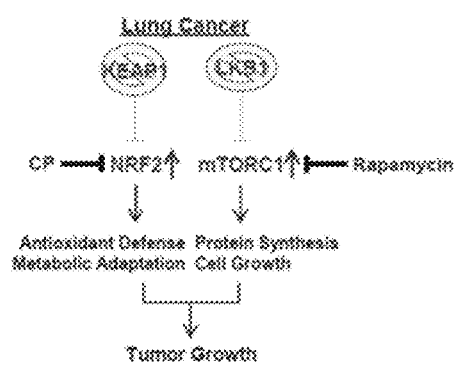

In contrast to the above results, as shown in FIGS. 7a and 7b, the cell growth inhibition of the H460 was slightly inhibited by treatment with clobetasol propionate and NRF2 knock-down even though it was a KEAP1 mutant cell line. Recent studies have shown that most KEAP1 mutations usually appears together with LKB1 mutations (A549, H460 cell lines) and that LKB1 mutations induce cancer cell growth through activation of mTORC1. Based on these conventional research results and the above results, as shown in FIG. 7c, the effect of clobetasol propionate was reduced in the H460 cell line because the H460 cell line had a KEAP1 mutation and an LKB1 mutation, so that NRF2 and mTORC1 were activated together, thereby making hypothesis, and it is anticipated that if NRF2 and mTORC1 can be inhibited, anticancer synergy effect will be obtained.

At first, cells were seeded on a plate coated with poly-HEMA (Sigma-Aldrich, St. Louis, USA) in order to compare activation of mTORC1 in H460 cell line and H460 cell line expressing LKB1-cDNA by transduction, and suspension culture was performed in a $CO_2$ incubator for 24 hours, and the activity of mTORC1 was measured by Western blotting in the same manner as in the Example 1.

Figure 7D:
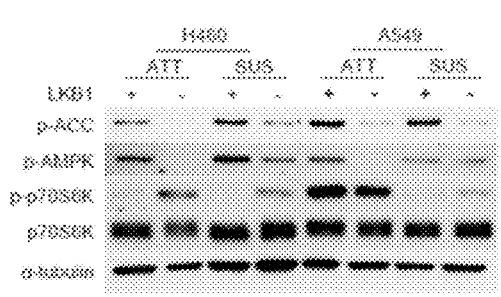

As a result, as shown in FIG. 7d, in case of the suspension culture of H460 cells, phosphorylation of p70S6K, mTORC1 substrate was increased in the absence of LKB1 expression compared with the presence of LKB1 expression. That is, it was known that the mTORC1 activity of H460 cells was high.

Thereafter, the synergistic effect was analyzed when clobetasol propionate and rapamycin were simultaneously treated, or NRF2 was knocked down using NRF2-shRNA and treated with rapamycin.

Figure 7E:
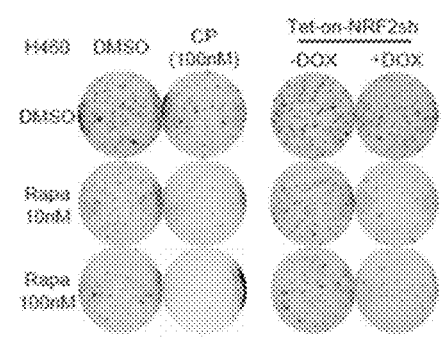

As a result, as shown in FIG. 7e, both the combination of clobetasol propionate and rapamycin and the combination of rapamycin treatment and suppression of NRF2 expression strongly inhibited the growth of H460 cells.

(3) In Vivo Experiments

On the other hand, xenograft assay was performed using A549 cell line. Specifically, Balb/c-nu mice (6-8 weeks of age, Orient Bio, Seongnam, Korea) were prepared to perform tumor genografts and A549-luc-C8 cells (Perkin Elmer, $5.0 \times 10^6$/head) were injected subcutaneously into the mice. Two weeks later, when the size of tumors reached 50-100 mm$^3$, mice were divided to 6 groups: a control group administered with only vehicle (200 µl of PBS containing 1.2% DMSO, 0.25% PEG 400 and 0.25% tween 80), a group administered with 0.5 mg/kg of clobetasol propionate (CP), a group administered with 1 mg/kg of clobetasol propionate, a group administered with 1 mg/kg of rapamycin, and Combination 1 (CP 0.5 mg/kg+rapamycin 1 mg/kg) and Combination 2 (CP 1 mg/kg+rapamycin 1 mg/kg). Then, for the next 40 days, the vehicle and rapamycin (n=5 per group) were injected intraperitoneally daily (5 days per week) and clobetasol propionate was injected intraperitoneally once every 2 days (3 days per week).

Primary tumor size and body weight were measured every 3 to 4 days by a caliper and a balance, and the volume of the tumor was V (mm$^3$)=(A×B$^2$)/2 (V is volume, A Is the long diameter and B is the short diameter).

Thereafter, mice were sacrificed in a 7.5% $CO_2$ chamber and tumors were obtained for further analysis. These studies were approved by the Institutional Animal Care and Use Committee (IACUC) of the National Cancer Center.

Figure 8A:
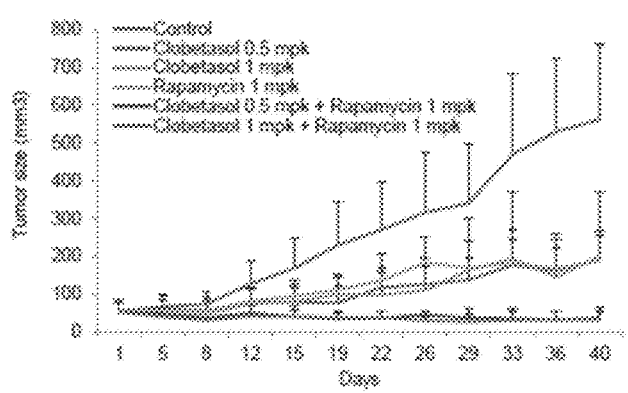
Figure 8B:
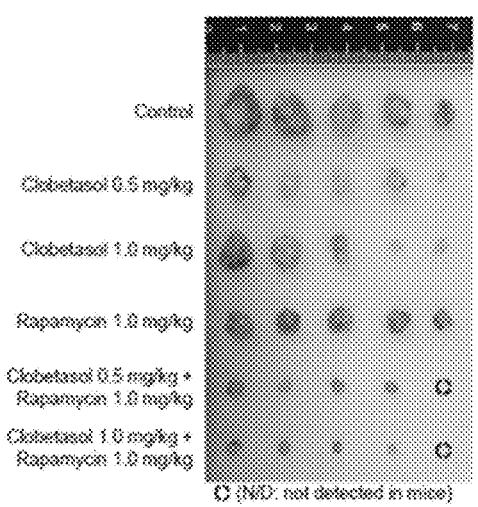
Figure 8C:
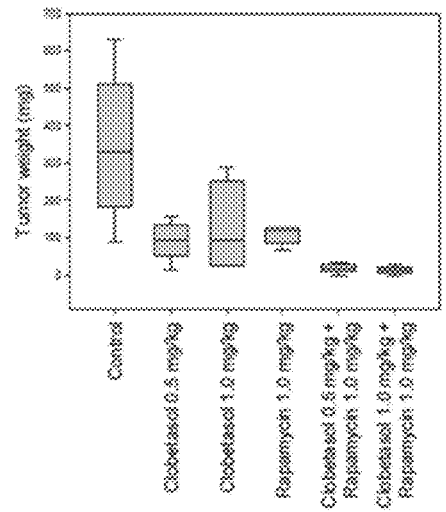
Figure 8D:
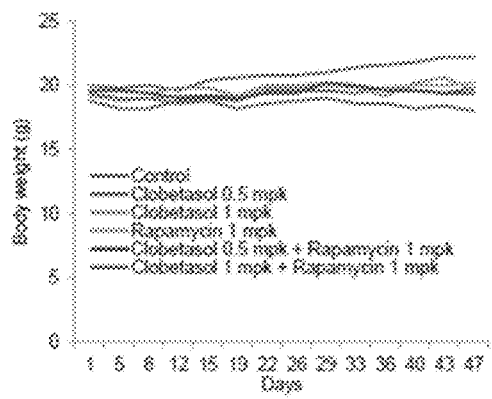

As a result, as shown in FIGS. 8a to 8c, a distinct anticancer effect was confirmed in the respective treatment with clobetasol propionate (0.5 mpk, 1 mpk) and rapamycin (1 mpk), especially, it was observed that very strong anticancer synergy effect that the tumor disappears during the combination treatment. While, as shown in FIG. 8d, there was no significant change in the body weight of the mice, therefore, there was no side effects.

Thus, in vivo, the combination of rapamycin and clobetasol propionate in the LKB1/KEAP1 mutant combination lung cancer cell lines was confirmed to have a strong anticancer synergy without side effects.

<Example 5> Synergistic Effect of Combined Use of Clobetasol Propionate and Sunitinib in Low Nutrient State (1) Measurement of NRF2 Expression Level of Normal Cells in Low Glucose State In the Example 3, it was generally confirmed that KEAP1 normal cells (H1299) maintained very low expression of NRF2 during cell culture, that is, sufficient nutrition (FIG. 6a). In order to confirm the change in the nutrient deficiency state (low glucose state), which is one of the representative features of the actual tumor microenvironment, Western blotting and luciferase experiment were carried out in the same manner as in the Example 1.

Figure 9A:
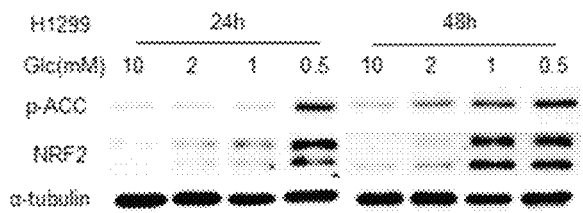
FIGS. 9a-9e show that NRF2 and AMPK (AMP-activated protein kinase) are activated in a nutrient deficient state, which is one of the characteristics of tumor microenvironment in KEAP1-normal/LKB1-normal lung cancer cell line and the in vitro anticancer synergistic effects of clobetasol propionate and AMPK inhibitor sunitinib when this lung cell line is cultured under low nutrient conditions.
Figure 9B:
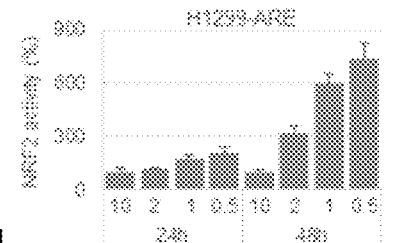

As a result, it was confirmed that NRF2 expression and activity were also increased in KEAP1 normal cells as shown in FIGS. 9a and 9b.

(2) Inhibitory Effect of NRF2 and AMPK Expression in Low Glucose State

Because as shown in FIG. 9a, it is known that LKB1 normal cells activate AMPK in low nutrient state (increased phosphorylation of ACC, a substrate of AMPK), and activation of AMPK increases the survival of cancer cells in a low nutritional state, the inhibition of both NRF2 and AMPK were expected to obtain strong synergistic effects. In order to confirm this, a cell line was established by transducing tet-on vector containing shRNA for AMPK and NRF2 into H1299 cell line and colony formation experiment was carried out in low nutrient state (glucose 2 mM). That is, the cells were seeded at a very low concentration in a 12-well plate and cultured in a medium containing 2 mM glucose for 2 weeks, and the degree of colony formation was observed by the crystal violet staining method as the same manner in the Example 3, and thus the anticancer effect was confirmed.

Figure 9C:
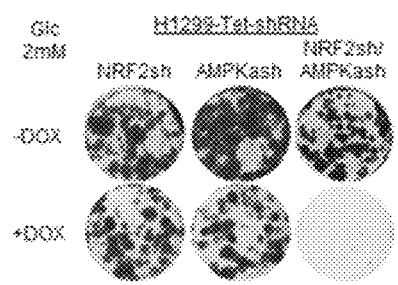

As a result, as shown in FIG. 9c, it was confirmed that when the AMPK and NRF2 expression were simultaneously inhibited, a very strong anticancer synergistic effect was exhibited.

(3) Combined Effect of Clobetasol Propionate and Sunitinib in Low Glucose State

Although there is no clinically available AMPK inhibitor to date, recent studies have found that the off target effect of sunitinib, a tyrosine kinase inhibitor (primarily inhibits VEGFR) used in the treatment of gastrointestinal stromal tumors, inhibits AMPK. Therefore, the same colony formation experiment as the above experiment was performed in a low nutrient state (glucose 2 mM) by treating sunitinib and clobetasol propionate together to observe the anticancer effect.

Figure 9D:
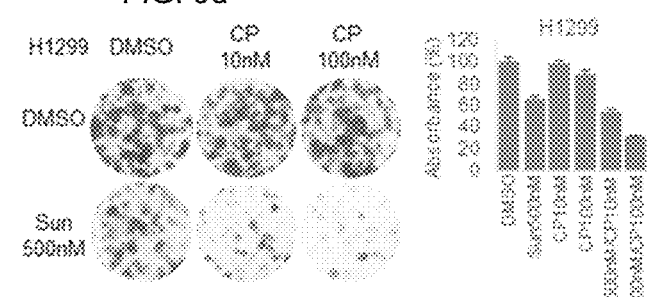

As a result, as shown in FIG. 9d, it was confirmed that a strong anticancer synergy effect was obtained when sunitinib and clobetasol propinonate were used in combination.

Figure 9E:
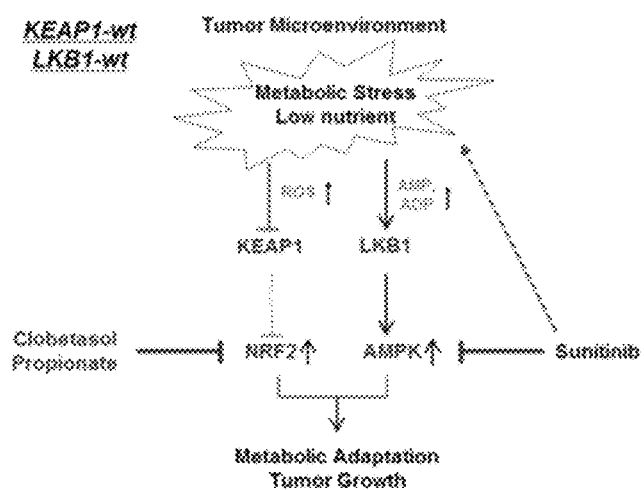

Thus, as shown in FIG. 9e, the both NRF2 and AMPK were activated in low nutrient state under real tumor microenvironment in normal KEAP1 and LKB1 cells, and the combined use of clobetasol propionate, i.e. glucocorticoids and AMPK inhibitor is very effective treatment method.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for treating lung cancer by inhibiting NRF2 activity in a subject having lung cancer with high NRF2 activity, comprising administering to the subject a composition comprising an effective amount of clobetasol propionate or mometasone furoate, wherein the clobetasol propionate or mometasone furoate inhibits NRF2 activity to treat the lung cancer with high NRF2 activity.

2. A method for treating lung cancer in a subject having lung cancer with high NRF2 and mTOR activities, comprising administering to the subject a composition comprising an effective amount of clobetasol propionate or mometasone furoate and a mTOR inhibitor, wherein the clobetasol propionate or mometasone furoate inhibits NRF2 activity to treat the lung cancer with high NRF2 and mTOR activities, and wherein the combination of clobetasol propionate or mometasone furoate and a mTOR inhibitor exhibits synergistic effect in treating the cancer.

3. The method of claim 2, wherein the mTOR inhibitor is at least one selected from the group consisting of rapamycin, temsirolimus, everolimus, ridaforolimus, AZD-8055, AZD-2014, OSI-027, INK128, PP242, NVP-BEZ235, XL765, BGT226 and PF-04691502.

4. The method of claim 2, wherein the composition is a pharmaceutical composition comprising 1 to 50 weight % of clobetasol propionate or mometasone furoate and 50 to 99 weight % of the mTOR inhibitor.

5. A method for treating lung cancer in a subject having lung cancer with high NRF2 and AMPK activities, comprising administering to the subject a composition comprising an effective amount of clobetasol propionate or mometasone furoate and an AMPK inhibitor, wherein the clobetasol propionate or mometasone furoate inhibits NRF2 activity to treat the lung cancer with high NRF2 and AMPK activities, and wherein the combination of clobetasol propionate or mometasone furoate and an AMPK inhibitor exhibits synergistic effect in treating the cancer.

6. The method of claim 5, wherein the AMPK inhibitor is at least one selected from the group consisting of sunitinib and dorsomorphin (compound C).

7. The method of claim 5, wherein the composition is a pharmaceutical composition comprising 1 to 50 weight % of clobetasol propionate or mometasone furoate and 50 to 99 weight % of the AMPK inhibitor.

* * * * *

SEQUENCE LISTING

<160> NUMBER OF SEQ ID NOS: 7

<210> SEQ ID NO 1
<211> LENGTH: 58
<212> TYPE: DNA
<213> ORGANISM: Artificial Sequence
<220> FEATURE:
<223> OTHER INFORMATION: shRNA

<400> SEQUENCE: 1
ccggagttga gcttcattga actgcctcga ggcagttcaa tgaagctcaa cttttttg      58

<210> SEQ ID NO 2
<211> LENGTH: 58
<212> TYPE: DNA
<213> ORGANISM: Artificial Sequence
<220> FEATURE:
<223> OTHER INFORMATION: shRNA

<400> SEQUENCE: 2
ccgggctcct actgtgatgt gaaatctcga gatttcacat cacagtagga gcttttg       58

<210> SEQ ID NO 3
<211> LENGTH: 58
<212> TYPE: DNA
<213> ORGANISM: Artificial Sequence
<220> FEATURE:
<223> OTHER INFORMATION: shRNA

<400> SEQUENCE: 3
ccggagagca agatttagat catttctcga gaaatgatct aaatcttgct cttttttg      58

<210> SEQ ID NO 4
<211> LENGTH: 20
<212> TYPE: DNA
<213> ORGANISM: Artificial Sequence
<220> FEATURE:
<223> OTHER INFORMATION: shRNA

<400> SEQUENCE: 4

```
cggtatgcaa caggacattg                                            20

<210> SEQ ID NO 5
<211> LENGTH: 20
<212> TYPE: DNA
<213> ORGANISM: Artificial Sequence
<220> FEATURE:
<223> OTHER INFORMATION: shRNA

<400> SEQUENCE: 5
actggttggg gtcttctgtg                                            20

<210> SEQ ID NO 6
<211> LENGTH: 18
<212> TYPE: DNA
<213> ORGANISM: Artificial Sequence
<220> FEATURE:
<223> OTHER INFORMATION: shRNA

<400> SEQUENCE: 6
tgccatccta aaagccac                                              18

<210> SEQ ID NO 7
<211> LENGTH: 21
<212> TYPE: DNA
<213> ORGANISM: Artificial Sequence
<220> FEATURE:
<223> OTHER INFORMATION: shRNA

<400> SEQUENCE: 7
tcaactggtc tcaagtcagt g                                          21
```